US008669421B2

(12) United States Patent
Gibson

(10) Patent No.: US 8,669,421 B2
(45) Date of Patent: Mar. 11, 2014

(54) DOVER LETTUCE VARIETY

(75) Inventor: George D. Gibson, Prunedale, CA (US)

(73) Assignee: Progeny Advanced Genetics, Salinas, CA (US)

( * ) Notice: Subject to any disclaimer, the term of this patent is extended or adjusted under 35 U.S.C. 154(b) by 255 days.

(21) Appl. No.: 13/177,449

(22) Filed: Jul. 6, 2011

(65) Prior Publication Data

US 2012/0030843 A1 Feb. 2, 2012

Related U.S. Application Data

(60) Provisional application No. 61/369,556, filed on Jul. 30, 2010.

(51) Int. Cl.

*A01H 1/00* (2006.01)
*A01H 4/00* (2006.01)
*A01H 5/00* (2006.01)
*A01H 5/10* (2006.01)
*C12N 15/82* (2006.01)

(52) U.S. Cl.

USPC ........... 800/305; 800/260; 800/278; 800/298; 435/410; 435/419; 435/430

(58) Field of Classification Search

None

See application file for complete search history.

(56) References Cited

U.S. PATENT DOCUMENTS

2012/0117677 A1* 5/2012 Knerr ........................... 800/260

* cited by examiner

*Primary Examiner* — Eileen B O Hara

(74) *Attorney, Agent, or Firm* — Morrison & Foerster LLP

(57) ABSTRACT

A new and distinct lettuce variety designated 'Dover' is described. 'Dover' is an iceberg lettuce variety exhibiting vigorous growth, increased weight, and increased yield. 'Dover' is also characterized as having a large head size, a short core length, and a longer harvest period.

11 Claims, No Drawings

DOVER LETTUCE VARIETY

CROSS REFERENCE TO RELATED APPLICATION

This application claims the benefit under 35 USC 119(e) of prior copending U.S. Provisional Patent Application No. 61/369,556, filed Jul. 30, 2010, the disclosure of which is hereby incorporated by reference in its entirety

FIELD

This invention relates to the field of plant breeding. In particular, this invention relates to a new lettuce, *Lactuca sativa* variety 'Dover'.

BACKGROUND

Lettuce is an increasingly popular crop. Worldwide lettuce consumption continues to increase. As a result of this demand, there is a continued need for new lettuce varieties. In particular, there is a need for improved iceberg lettuce varieties that exhibit vigorous growth, increased weight and yield.

SUMMARY

In order to meet these needs, the present invention is directed to an improved iceberg lettuce variety that exhibits vigorous growth, increased weight, and increased yield. In particular, the present invention is directed to *Lactuca sativa* seed designated as 'Dover' having ATCC Accession Number PTA-12097. The present invention is further directed to a *Lactuca sativa* plant produced by growing 'Dover' lettuce seed having ATCC Accession Number PTA-12097. The present invention is further directed to a *Lactuca sativa* plant having all the physiological and morphological characteristics of a *Lactuca sativa* plant produced by growing 'Dover' lettuce seed having ATCC Accession Number PTA-12097. The present invention is further directed to an $F_1$ hybrid *Lactuca sativa* plant having 'Dover' as a parent where 'Dover' lettuce seed is grown from 'Dover' seed having ATCC Accession Number PTA-12097.

The present invention is further directed to pollen and ovules produced by 'Dover' lettuce plants. The present invention is further directed to tissue culture of 'Dover' lettuce plants.

The present invention is further directed to a method of selecting lettuce including: a) growing 'Dover' lettuce plants where the plants are grown from lettuce seed having ATCC Accession Number PTA-12097, and b) selecting a plant from step a). The present invention is further directed to lettuce plants and seeds produced by the selected lettuce plants.

The present invention is further directed to a method of breeding lettuce comprising crossing a lettuce plant with a plant grown from 'Dover' lettuce seed having ATCC Accession Number PTA-12097. The present invention is further directed to lettuce plants and seeds produced where the lettuce plant is produced by the breeding method of the invention.

BRIEF DESCRIPTION OF THE TABLES

Table 1 shows trial data comparing core lengths of 'Crusader' and 'Dover' iceberg lettuce varieties.

Table 2 shows trial data comparing head diameters of 'Crusader' and 'Dover' iceberg lettuce varieties.

DETAILED DESCRIPTION

In order to more clearly understand the invention, the following definitions are provided:

Iceberg Lettuce:

Iceberg lettuce, *Lactuca sativa* L. var. *capitala* L. is also known as 'crisp head' lettuce. Iceberg lettuce is a lettuce plant type that forms a firm, spherical head formed with tightly folded brittle textured foliage. Internal color ranges from white to yellow to light green. The wrapper leaves surrounding the head are wider than they are long. Leaf margins can vary by type, being entire, undulating, or frilled. Wrapper leaf color ranges from yellow green to dark green.

Core Length:

Core length is the length of the internal lettuce stem. Core length is measured from the base of the cut head to the tip of the core.

Head Diameter:

Head diameter is the diameter of the vertically sliced lettuce plant head at its widest horizontal point, perpendicular to the stem.

Frame Diameter:

The frame diameter is a measurement of the lettuce plant diameter at its widest point. The measurement of frame diameter is from the outer most wrapper leaf tip to outer most wrapper leaf tip.

Head Weight:

Weight of the marketable lettuce plant, cut and trimmed to market specifications.

Rogueing:

Rogueing is the process in seed production where undesired plants are removed from a variety. The plants are removed since they differ physically from the general desired expressed characteristics of the variety. The differences can be related to size, color, maturity, leaf texture, leaf margins, growth habit, or any other characteristic that distinguishes the plant.

Market Stage:

Market stage is the stage when a lettuce plant is ready for commercial lettuce harvest. In the case of an iceberg variety, the head is solid, and has reached an adequate size and weight.

Taking into account these definitions, the present invention is directed to seeds of the lettuce variety 'Dover', plants produced by growing 'Dover' seeds, plants selected from a collection of 'Dover' plants and seeds derived or produced from plants produced by crossing a lettuce plant with a 'Dover' lettuce plant and seeds derived or produced from these plants.

Origin and Breeding History of the Variety 'Dover'

'Dover' is a Vanguard type iceberg lettuce variety developed from a hand pollinated cross of the cultivars 'Raider' and 'Fall Green'. The initial cross was made in our San Joaquin valley research and development seed production field in year 1. The F1 seed harvested was designated as #935550. 'Raider', a medium sized heavily textured vanguard type iceberg lettuce was selected as a source of heat tolerance, adaptability for the fall harvest period in the desert south west, and bolting and tip burn resistance. 'Fall Green' was selected for its improved vigor, darker size color and bolting tolerance. By implementation of the pedigree selection breeding method, a larger heading was developed that was a more widely adapted vanguard type iceberg lettuce variety with excellent resistance to tip burn, and bolting for fall harvest in the desert south west and Huron lettuce production regions.

Approximately 50 plants of the $F_1$ seed were planted in a San Joaquin Valley Calif. research seed production field for seed increase in year 2. The $F_2$ seed was harvested in mass in August of year 2, and labeled 94144.

An $F_2$ population of 94144 was planted in a research and development field trial in Yuma, Ariz. in late year 2. Individual $F_2$ plants were selected at market maturity specifically for larger heading iceberg types with shorter cores and improved resistance to tip burn. The particular individual plant selection labeled 94133-4 was noted to demonstrate the desired traits, with improved head size, was slower bolting, and did not show any signs of tip burn. The selected plants were removed from the trial, and allowed to fully mature in a green house facility. The $F_3$ seed from the selections were harvested in the early spring of year 3.

The $F_3$ seed from the single plant was then planted in a research and development seed production crop in the San Joaquin Valley in year 5, evaluated, and additional individual plants were selected. The individual plants that were selected demonstrated the desired Salinas type, improved leaf texture, were slower bolting, and did not show any signs of tip burn. These individual plants were flagged in the field, allowed to grow to full maturity, and the $F_4$ seed from each was harvested individually.

The $F_4$ lines from the individual plant selections were included in a research and development plot trial in the fall of year 7 in Yuma, Ariz. The $F_4$ lines were evaluated at market maturity and additional individual plant selections were made based on the attributes described above. The selected plants were labeled and removed from the research plot trial and allowed to grow to full maturity in a greenhouse facility. The $F_5$ seed from the individual plant selections was harvested.

The $F_5$ lines from the individual plant selections were included in a research and development plot trial in the fall of year 9 in the Yuma, Ariz. production region to screen for type, uniformity, and demonstration of the selected traits. The $F_5$ lines were evaluated at market maturity and individual plant selections were made for improved vigor, improved texture, and improved size. All individual plants that were largest heading, slowest to bolt, and free of tip burn were selected, removed from the research plot trial, and allowed to grow to full maturity in a greenhouse facility. The $F_6$ seed from the individual plant selections was harvested. Included among the selections was a single plant labeled RYM01080 47-1 B.

The $F_6$ selections were then increased in year 11 in a research and development seed production nursery in the San Joaquin Valley, Calif. The $F_6$ lines were evaluated and selectively rogued for uniformity in size, type, and maturity. The $F_7$ seed from each line was mass harvested. The $F_7$ lines were evaluated in trials in the fall of year 12 in the desert south west lettuce production region, and plant number PSJV031634 was noted to best demonstrate the combined attributes. PSJV031364 was clearly a uniform iceberg lettuce variety, with improved head and frame size, slower bolting, and had a higher resistance to tip burn than the commercial standards and sister lines.

PSJV031634 was then increased in year 13 at a research and development seed production block in the San Joaquin Valley, Calif. where it was noted to be uniform, stable, and free of variants. The $F_8$ seed was harvested in mass in the late summer of year 13, identified as PSJV054025. PSJV054025 was trialed in multiple times and locations throughout the desert south west and the Huron production regions for the fall harvest slot in the year 14 growing season, where it continued to out perform commercial standard varieties and other research lines in development. Based on these results, the plant was advanced and designated as PX 1569 in March of year 15.

PX 1569 was increased in year 15 in a research and development seed production block in the San Joaquin Valley, Calif. The variety was evaluated and noted to be uniform, stable, and free of variants. The $F_9$ seed was harvested in mass in the late summer of year 15. Additional trialing of $F_9$ seed for spring harvest in the desert south west was conducted in year 16.

Seed from PX 1569 was designated 'Dover'.

As evaluated in seed production and field trials the $F_8$, the $F_9$, and the $F_{10}$ seed from the variety 'Dover' has been uniform and stable without variants.

A. Variety Description Information

| Plant Type: | Iceberg |
|---|---|
| Seed: | |
| Seed Color: | Black |
| Light Dormancy: | No |
| Heat Dormancy: | Yes |
| Cotyledons: | |
| Shape of Cotyledons: | Intermediate |
| Shape of Fourth Leaf: | Intermediate |
| Length/Width Index of Fourth Leaf: | 26 |
| Apical Margin: | Finley Dentate |
| Basal Margin: | Finley Dentate |
| Undulation: | Slight |
| Green Color: | Dark |
| Anthocyanin: | Absent |
| Distribution: | None |
| Rolling: | Absent |
| Cupping: | Uncupped |
| Reflexing: | None |
| Mature Leaves: | |
| Margin: | |
| Incision Depth (Deepest penetration of the margin): | Moderate |
| Indentation (Finest Division of the Margin): | Crenate |
| Undulation of the Apical Margin: | Absent |
| Green Color: | Dark |
| Anthocyanin | |
| Distribution: | None |
| Size: | Large |
| Glossiness: | Moderate |
| Blistering: | Moderate |
| Leaf Thickness: | Thick |
| Trichomes: | Absent |

B. Comparison to Most Similar Variety

| Characteristic | Dover | Crusader |
|---|---|---|
| Spread of Frame Leaves | 62 cm | 56 cm |
| Head Diameter (market trimmed with single cup leaf) | 15 cm | 13 cm |
| Head Shape | Spherical | Spherical |
| Head Size Class | large | Large |
| Head Count per Carton | 24 | 24 |
| Head Weight | 969 grams | 802 grams |
| Head Firmness | Firm | Firm |
| Butt | | |
| Shape | Rounded | Rounded |
| Midrib | Moderately Raised | Moderately Raised |

-continued

| Characteristic | Dover | Crusader |
|---|---|---|
| Core (Stem of Market-trimmed Head) | | |
| Diameter at the base of the Head | 42 mm | 40 mm |
| Ratio of Head Diameter/Core Diameter | 3.3 | 3.2 |
| Core Height from base of Head to Apex | 40 mm | 46 mm |
| Number of Days from First Water Date to Seed Stalk Emergence (Summer condition) | 64 | 63 |
| Bolting Class | Medium | Medium |
| Height of Mature Seed Stalk | 108 cm | 109 cm |
| Spread of Bolter Plant | 32 cm | 32 cm |
| Bolter Leaves | Curved | Curved |
| Margin | Dentate | Dentate |
| Color | Medium Green | Medium Green |
| Bolter Habit | | |
| Terminal Inflorescence | Present | Present |
| Lateral Shoots (above head) | Present | Present |
| Basal Side Shoots | Absent | Absent |
| Adaptation Regions | Desert South West | Desert South West |

C. Growing Season

| Season | Dover | Crusader |
|---|---|---|
| Spring area | Not Adapted | Not Adapted |
| Summer area | Not Adapted | Not Adapted |
| Fall area | Huron CA, Desert South West | Huron CA, Desert South West |
| Winter area: | Not Adapted | Not Adapted |

D. Diseases and Stress Reactions

| Disease or Stress | Dover | Crusader |
|---|---|---|
| Virus | | |
| Big Vein: | Susceptible | Susceptible |
| Lettuce Mosaic: | Resistant | Resistant |

E. Fungi/Bacteria

| Fungal/Bacterial | Dover | Crusader |
|---|---|---|
| Corky Root Rot (*Pythium* Root Rot): | Susceptible | Susceptible |
| Downy Mildew (Races I, IIA, III): | Susceptible | Susceptible |
| Powdery Mildew: | Susceptible | Susceptible |
| Sclerotinia Rot: | Susceptible | Susceptible |
| Bacterial Soft Rot (*Pseudomonas* spp. & others): Not tested | Susceptible | Susceptible |
| Botrytis (Gray Mold): | Susceptible | Susceptible |
| Other: Corky Root Rot (*Rhizomonas suberifaciens*): | Susceptible | Susceptible |

F. Insects

| Insects | Dover | Crusader |
|---|---|---|
| Cabbage Loopers: | Susceptible | Susceptible |
| Root Aphids: | Susceptible | Susceptible |
| Green Peach Aphid: | Susceptible | Susceptible |

G. Physiological/Stress

| Stress | Dover | Crusader |
|---|---|---|
| Tipburn | Resistant | Resistant |
| Heat | Resistant | Resistant |
| Drought | Susceptible | Susceptible |
| Cold | Susceptible | Susceptible |
| Salt | Susceptible | Susceptible |

H. Post Harvest

| Characteristic | Dover | Crusader |
|---|---|---|
| Pink Rib | Moderately Susceptible | Moderately Susceptible |
| Russet Spotting | Moderately Susceptible | Moderately Susceptible |
| Rusty Brown Discoloration | Moderately Susceptible | Moderately Susceptible |
| Internal Rib Necrosis (Blackheart, Gray Rib, Gray Streak) | Moderately Susceptible | Moderately Susceptible |

Breeding and Selection

The present invention is further directed to the use of 'Dover' lettuce in breeding and selection of new varieties.

A. Breeding

In lettuce breeding, lines are selected for their appropriate characteristics. For example, one line may be selected for bolt tolerance in the fall growing conditions of the desert production locations of California and Arizona. Another line may be selected for the size, color, and texture of the lettuce head. Crosses are made, for example, to produce a dark green, sure heading iceberg lettuce with improved texture, and size for fall plantings in Yuma Ariz. and Huron Calif.

To optimize crossing, it is important to note that lettuce is an obligate self-pollinating species. This means that the pollen is shed before stigma emergence, assuring 100% self-fertilization. Since each lettuce flower is an aggregate of about 10-20 individual florets (typical of the Compositae family), manual removal of the anther tubes containing the pollen may be performed by procedures well known in the art of lettuce breeding.

In addition to manual removal of anther tubes, a modified method of misting to wash the pollen off prior to fertilization may be used to assure crossing or hybridization. About 60-90 minutes past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen are washed off with enough pressure to dislodge the pollen grains, but not enough to damage the style. Excess water is dried off with clean paper towels. About 30 minutes later, the styles should spring back up and the two lobes of the stigma are visibly open in a "V" shape. Pollen from another variety or donor parent is then introduced by gently rubbing the stigma and style of the donor parent to the maternal parent. Tags with the pertinent information on date and pedigree are then secured to the flowers.

About 2-3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two useful references teaching the methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907-908.

B. Selection

In addition to crossing, selection may be used to isolate lettuce new lettuce lines. One or more lettuce seeds are planted, the plants are grown, and single plant selections are made of plants with desired characteristics. Such characteristics may include improved head and frame size, deeper or darker green leaf color, etc. Seed from the single plant selections are harvested; separated from seeds of the other plants in the field, and re-planted. The plants from the selected seed are monitored to determine if they exhibit the desired characteristics from the originally selected line. Selection work is continued over multiple generations to increase the uniformity and size of new line.

DEPOSIT INFORMATION

Applicants have made available to the public without restriction a deposit of at least 2500 seeds of lettuce variety 'Dover' with the American Type Culture Collection (ATCC), Rockville, Md. 20852 with a deposit on Sep. 19, 2011 which has been assigned ATCC number PTA-12097. This deposit of the lettuce variety 'Dover' will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801-1.809, including providing an indication of the viability of the sample. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Cultivar Protection Act (7 USC 2321 et seq.).

The deposit will be maintained in the ATCC depository, which is a public depository, for a period of 30 years, or 5 years after the most recent request, or for the effective life of the patent, whichever is longer, and will be replaced if a deposit becomes nonviable during that period.

This invention will be better understood by reference to the following non-limiting Examples.

EXAMPLES

Example 1

General Trialing Method

I. Set Up
1. Parental lines and competing varieties are identified.
2. Primary slots are identified.
3. Necessary accession lines are located and purchased/received from seed dealers or growers.
4. All varieties are assigned a number to maintain integrity and anonymity.
5. Trials are set up in with all necessary varieties. Variety arrangement for trial is diagramed.

II. Planting
1. Commercial plantings are located by contacting commercial growers during the planting slot recommended for the variety.
2. A field is located during commercial planting, and the necessary rows and area are marked off.
3. Varieties are planted according to a diagram in 100 ft. ranges.
4. All varieties are planted in same manner to mimic the planting of the commercial variety as closely as possible.
5. A trial map is drawn diagramming the trial, the trial location in the field and directions to the field.

III. Maintenance
1. All varieties are treated identically. Plants are watered, fertilized, and treated to control pests in the same manner as the commercial field.
2. The trial is thinned to separate the plants for optimum growth.

Example 2

Comparative Analysis

Following the procedures of Example 1, 'Dover' iceberg lettuce was compared to its most similar variety. The data are presented in Tables 1 and 2. Table 1 shows trial data comparing core lengths of 'Crusader' and 'Dover' iceberg lettuce varieties. Table 2 shows trial data comparing head diameters of 'Crusader' and 'Dover' iceberg lettuce varieties.

TABLE 1

Evaluation of Dover and most similar variety Crusader for Core Length

| Map No. | SSJ09266 | | SSJ09270 | | SSJ09271 | |
|---|---|---|---|---|---|---|
| Trial No. | 1 | | 2 | | 3 | |
| Wet Date/Eval Date (month/day) | 08/29 | 11/03 | 08/29 | 11/03 | 08/29 | 11/05 |
| Location | Huron CA | | Huron CA | | Huron CA | |
| Map No. | SYM09319 | | SYM09327 | | SYM09340 | |
| Trial No. | 4 | | 5 | | 6 | |
| Wet Date/Eval Date (month/day) | 09/24 | 12/16 | 09/25 | 12/19 | 10/02 | 10/02 |
| Location | Yuma AZ | | Yuma AZ | | Yuma AZ | |

TABLE 1-continued

Evaluation of Dover and most similar variety Crusader for Core Length

| Plant | Core Length (mm) | | Core Length (mm) | | Core Length (mm) | |
|---|---|---|---|---|---|---|
| | Dover | Crusader | Dover | Crusader | Dover | Crusader |
| 1 | 35.0 | 40.0 | 45.0 | 45.0 | 45.0 | 45.0 |
| 2 | 35.0 | 40.0 | 45.0 | 45.0 | 45.0 | 45.0 |
| 3 | 35.0 | 45.0 | 45.0 | 45.0 | 50.0 | 45.0 |
| 4 | 30.0 | 40.0 | 40.0 | 45.0 | 45.0 | 45.0 |
| 5 | 30.0 | 35.0 | 40.0 | 45.0 | 45.0 | 50.0 |
| 6 | 30.0 | 40.0 | 40.0 | 45.0 | 45.0 | 55.0 |
| 7 | 30.0 | 40.0 | 40.0 | 45.0 | 50.0 | 55.0 |
| 8 | 30.0 | 35.0 | 45.0 | 45.0 | 50.0 | 45.0 |
| 9 | 30.0 | 40.0 | 45.0 | 50.0 | 50.0 | 55.0 |
| 10 | 30.0 | 35.0 | 40.0 | 50.0 | 45.0 | 55.0 |
| 11 | 30.0 | 35.0 | 40.0 | 45.0 | 50.0 | 55.0 |
| 12 | 35.0 | 35.0 | 35.0 | 50.0 | 45.0 | 60.0 |
| 13 | 25.0 | 40.0 | 35.0 | 55.0 | 50.0 | 65.0 |
| 14 | 30.0 | 35.0 | 40.0 | 55.0 | 55.0 | 60.0 |
| 15 | 25.0 | 30.0 | 45.0 | 55.0 | 55.0 | 60.0 |
| 16 | 30.0 | 35.0 | 45.0 | 50.0 | 55.0 | 55.0 |
| 17 | 25.0 | 35.0 | 40.0 | 55.0 | 45.0 | 45.0 |
| 18 | 25.0 | 40.0 | 35.0 | 45.0 | 45.0 | 45.0 |
| 19 | 30.0 | 40.0 | 45.0 | 40.0 | 40.0 | 45.0 |
| 20 | 30.0 | 45.0 | 40.0 | 40.0 | 40.0 | 45.0 |
| 21 | 30.0 | 40.0 | 40.0 | 40.0 | 35.0 | 45.0 |
| 22 | 30.0 | 40.0 | 35.0 | 40.0 | 35.0 | 45.0 |
| 23 | 35.0 | 45.0 | 35.0 | 40.0 | 30.0 | 45.0 |
| 24 | 35.0 | 35.0 | 30.0 | 40.0 | 35.0 | 40.0 |
| 25 | 35.0 | 35.0 | 30.0 | 40.0 | 40.0 | 35.0 |
| 26 | 30.0 | 35.0 | 45.0 | 45.0 | 45.0 | 45.0 |
| 27 | 30.0 | 35.0 | 30.0 | 35.0 | 40.0 | 45.0 |
| 28 | 30.0 | 40.0 | 45.0 | 40.0 | 45.0 | 50.0 |
| 29 | 30.0 | 45.0 | 45.0 | 40.0 | 40.0 | 55.0 |
| 30 | 25.0 | 45.0 | 35.0 | 40.0 | 35.0 | 55.0 |
| Average | 30.3 | 38.5 | 39.8 | 45.0 | 44.3 | 49.7 |
| Stan dev | 3.20E+00 | 3.97E+00 | 5.00E+00 | 5.41E+00 | 6.40E+00 | 6.94E+00 |
| T test | 1.22E−05 | | 3.06E−04 | | 3.03E−03 | |
| Probability % | 100.0 | | 99.9694 | | 99.6972 | |
| % Difference | −21.2 | | −11.5 | | −10.7 | |
| Confidence Int | 0.0366 | 0.0455 | 0.0572 | 0.0620 | 0.0732 | 0.0795 |
| Range of Var min* | 30.30 | 38.45 | 39.78 | 44.94 | 44.26 | 49.59 |
| Range of Var max* | 30.37 | 38.55 | 39.89 | 45.06 | 44.41 | 49.75 |

| Plant | Core Length (mm) | | Core Length (mm) | | Core Length (mm) | |
|---|---|---|---|---|---|---|
| | Dover | Crusader | Dover | Crusader | Dover | Crusader |
| 1 | 45.0 | 50.0 | 55.0 | 55.0 | 30.0 | 30.0 |
| 2 | 45.0 | 45.0 | 55.0 | 55.0 | 25.0 | 30.0 |
| 3 | 45.0 | 45.0 | 55.0 | 55.0 | 30.0 | 35.0 |
| 4 | 40.0 | 45.0 | 50.0 | 55.0 | 25.0 | 35.0 |
| 5 | 40.0 | 50.0 | 50.0 | 55.0 | 25.0 | 35.0 |
| 6 | 40.0 | 50.0 | 50.0 | 55.0 | 30.0 | 35.0 |
| 7 | 45.0 | 50.0 | 50.0 | 55.0 | 30.0 | 35.0 |
| 8 | 40.0 | 50.0 | 55.0 | 55.0 | 35.0 | 30.0 |
| 9 | 40.0 | 55.0 | 45.0 | 50.0 | 35.0 | 35.0 |
| 10 | 35.0 | 55.0 | 55.0 | 50.0 | 35.0 | 30.0 |
| 11 | 35.0 | 55.0 | 45.0 | 50.0 | 35.0 | 30.0 |
| 12 | 45.0 | 60.0 | 45.0 | 55.0 | 35.0 | 30.0 |
| 13 | 45.0 | 55.0 | 45.0 | 55.0 | 35.0 | 35.0 |
| 14 | 50.0 | 60.0 | 40.0 | 50.0 | 25.0 | 35.0 |
| 15 | 50.0 | 60.0 | 40.0 | 50.0 | 35.0 | 35.0 |
| 16 | 50.0 | 45.0 | 40.0 | 55.0 | 40.0 | 35.0 |
| 17 | 55.0 | 50.0 | 40.0 | 60.0 | 35.0 | 35.0 |
| 18 | 55.0 | 50.0 | 45.0 | 55.0 | 25.0 | 30.0 |
| 19 | 50.0 | 50.0 | 50.0 | 65.0 | 25.0 | 30.0 |
| 20 | 55.0 | 50.0 | 50.0 | 55.0 | 25.0 | 30.0 |
| 21 | 55.0 | 55.0 | 55.0 | 55.0 | 30.0 | 35.0 |
| 22 | 45.0 | 55.0 | 55.0 | 50.0 | 25.0 | 35.0 |
| 23 | 45.0 | 55.0 | 45.0 | 65.0 | 30.0 | 35.0 |
| 24 | 40.0 | 60.0 | 45.0 | 60.0 | 30.0 | 35.0 |
| 25 | 45.0 | 55.0 | 40.0 | 55.0 | 30.0 | 35.0 |
| 26 | 55.0 | 60.0 | 55.0 | 55.0 | 30.0 | 35.0 |
| 27 | 55.0 | 55.0 | 40.0 | 55.0 | 30.0 | 35.0 |
| 28 | 45.0 | 55.0 | 45.0 | 60.0 | 25.0 | 35.0 |
| 29 | 45.0 | 60.0 | 45.0 | 65.0 | 25.0 | 35.0 |
| 30 | 45.0 | 55.0 | 40.0 | 50.0 | 25.0 | 30.0 |

TABLE 1-continued

| Evaluation of Dover and most similar variety Crusader for Core Length | | | | | | |
|---|---|---|---|---|---|---|
| Average | 46.0 | 53.2 | 47.5 | 55.3 | 29.8 | 33.3 |
| Stan dev | 5.93E+00 | 4.82E+00 | 5.69E+00 | 4.34E+00 | 4.45E+00 | 2.40E+00 |
| T test | 3.43E−06 | | 1.38E−07 | | 3.57E−04 | |
| Probability % | 99.9997 | | 100.0000 | | 99.9643 | |
| % Difference | −13.5 | | −14.2 | | −10.5 | |
| Confidence Int | 0.0679 | 0.0552 | 0.0651 | 0.0497 | 0.0509 | 0.0274 |
| Range of Var min* | 45.93 | 53.11 | 47.43 | 55.28 | 29.78 | 33.31 |
| Range of Var max* | 46.07 | 53.22 | 47.57 | 55.38 | 29.88 | 33.36 |

*Range of variation among means of statistically significant differences at the 95% level using the confidence interval

TABLE 2

| Evaluation of Dover and most similar variety Crusader for size of Head Diameter | | | | | | |
|---|---|---|---|---|---|---|
| Map No. | SSJ09266 | | SSJ09270 | | SSJ09271 | |
| Trial No. | 1 | | 2 | | 3 | |
| Wet Date/ Eval Date (month/day) | 08/29 | 11/03 | 08/29 | 11/03 | 08/29 | 11/05 |
| Location | Huron CA | | Huron CA | | Huron CA | |
| Map No. | SYM09319 | | SYM09327 | | SYM09340 | |
| Trial No. | 4 | | 5 | | 6 | |
| Wet Date/ Eval Date (month/day) | 09/24 | 12/16 | 09/25 | 12/19 | 10/02 | 10/02 |
| Location | Yuma AZ | | Yuma AZ | | Yuma AZ | |
| | Head Diameter (cm) | | Head Diameter (cm) | | Head Diameter (cm) | |
| Plant | Dover | Crusader | Dover | Crusader | Dover | Crusader |
| 1 | 15.5 | 14.0 | 15.5 | 14.0 | 15.0 | 13.0 |
| 2 | 16.0 | 14.0 | 15.5 | 14.0 | 15.0 | 13.0 |
| 3 | 15.5 | 14.0 | 16.0 | 14.5 | 15.5 | 13.0 |
| 4 | 15.5 | 15.0 | 16.0 | 15.0 | 15.5 | 13.0 |
| 5 | 16.0 | 14.0 | 16.0 | 14.5 | 15.5 | 13.5 |
| 6 | 16.0 | 14.0 | 16.0 | 14.5 | 13.0 | 12.5 |
| 7 | 16.0 | 14.0 | 16.0 | 14.0 | 15.5 | 12.0 |
| 8 | 16.0 | 15.5 | 15.5 | 13.0 | 13.0 | 12.0 |
| 9 | 15.5 | 13.5 | 15.5 | 13.0 | 15.5 | 13.0 |
| 10 | 15.0 | 13.5 | 16.0 | 14.0 | 14.0 | 13.0 |
| 11 | 15.0 | 13.0 | 16.0 | 13.0 | 14.0 | 13.0 |
| 12 | 14.5 | 13.0 | 15.5 | 13.0 | 14.5 | 13.0 |
| 13 | 15.0 | 13.0 | 15.0 | 13.5 | 14.5 | 12.0 |
| 14 | 15.0 | 13.5 | 15.0 | 14.0 | 15.0 | 12.0 |
| 15 | 15.5 | 13.5 | 15.0 | 14.0 | 15.0 | 12.5 |
| 16 | 15.5 | 13.5 | 15.5 | 13.5 | 15.0 | 12.5 |
| 17 | 16.0 | 13.5 | 15.5 | 13.5 | 15.5 | 12.0 |
| 18 | 14.0 | 14.0 | 16.0 | 13.5 | 15.5 | 12.0 |
| 19 | 15.0 | 15.0 | 15.0 | 13.0 | 14.0 | 12.0 |
| 20 | 14.0 | 1.4 | 15.0 | 13.0 | 14.0 | 12.5 |
| 21 | 14.0 | 13.5 | 15.5 | 13.0 | 14.5 | 12.5 |
| 22 | 15.0 | 15.0 | 16.0 | 13.0 | 14.5 | 12.0 |
| 23 | 15.0 | 15.0 | 15.5 | 13.5 | 14.5 | 12.0 |
| 24 | 15.5 | 13.5 | 15.0 | 13.5 | 15.0 | 12.0 |
| 25 | 15.5 | 13.5 | 15.0 | 15.0 | 15.0 | 12.0 |
| 26 | 15.0 | 14.0 | 14.0 | 13.5 | 14.0 | 12.5 |
| 27 | 16.0 | 14.0 | 14.0 | 14.0 | 15.0 | 12.5 |
| 28 | 16.0 | 14.5 | 15.5 | 14.0 | 15.0 | 12.5 |
| 29 | 15.5 | 13.5 | 14.0 | 13.0 | 15.0 | 12.0 |
| 30 | 15.5 | 13.0 | 15.5 | 13.0 | 15.0 | 12.0 |
| Average | 15.3 | 13.5 | 15.4 | 13.7 | 14.7 | 12.5 |
| Stan dev | 6.09E−01 | 2.38E+00 | 5.97E−01 | 6.21E−01 | 6.91E−01 | 4.61E−01 |
| T test | 1.34E−04 | | 1.08E−15 | | 1.11E−21 | |
| Probability % | 99.99 | | 100.00 | | 100.00 | |
| % Difference | −13.6 | | −12.6 | | −18.3 | |
| Confidence Int | 0.0070 | 0.0273 | 0.0068 | 0.0071 | 0.0079 | 0.0053 |
| Range of Var min* | 15.31 | 13.45 | 15.38 | 13.66 | 14.73 | 12.44 |
| Range of Var max* | 15.32 | 13.51 | 15.39 | 13.67 | 14.74 | 12.46 |

TABLE 2-continued

Evaluation of Dover and most similar variety Crusader for size of Head Diameter

| Plant | Head Diameter (cm) | | Head Diameter (cm) | | Head Diameter (cm) | |
|---|---|---|---|---|---|---|
| | Dover | Crusader | Dover | Crusader | Dover | Crusader |
| 1 | 15.5 | 13.5 | 15.0 | 13.0 | 15.0 | 12.0 |
| 2 | 15.5 | 13.5 | 15.0 | 13.5 | 16.0 | 12.0 |
| 3 | 15.0 | 13.5 | 15.0 | 13.0 | 14.0 | 11.0 |
| 4 | 16.0 | 15.0 | 15.0 | 13.5 | 14.0 | 12.0 |
| 5 | 16.0 | 13.5 | 15.0 | 12.5 | 14.5 | 12.0 |
| 6 | 16.0 | 13.5 | 15.0 | 13.0 | 14.5 | 12.0 |
| 7 | 16.0 | 13.5 | 15.5 | 13.0 | 15.0 | 12.0 |
| 8 | 15.5 | 14.0 | 15.5 | 13.0 | 15.0 | 11.0 |
| 9 | 16.0 | 14.0 | 14.0 | 13.5 | 15.0 | 11.0 |
| 10 | 16.0 | 13.5 | 15.5 | 12.0 | 14.5 | 10.5 |
| 11 | 16.0 | 13.5 | 16.0 | 12.0 | 14.0 | 10.5 |
| 12 | 16.0 | 14.0 | 15.5 | 14.0 | 14.0 | 11.0 |
| 13 | 16.5 | 14.0 | 15.5 | 14.0 | 14.0 | 10.5 |
| 14 | 16.5 | 13.5 | 15.5 | 14.0 | 14.0 | 11.0 |
| 15 | 15.0 | 14.0 | 14.0 | 13.0 | 14.0 | 11.0 |
| 16 | 15.0 | 14.0 | 14.0 | 12.5 | 15.0 | 12.0 |
| 17 | 15.0 | 13.5 | 14.4 | 13.5 | 14.5 | 10.0 |
| 18 | 15.0 | 13.5 | 15.0 | 13.5 | 15.0 | 10.5 |
| 19 | 15.0 | 13.5 | 15.0 | 12.0 | 15.0 | 12.0 |
| 20 | 15.5 | 13.5 | 15.5 | 12.0 | 15.0 | 12.0 |
| 21 | 15.0 | 14.0 | 16.0 | 13.5 | 14.5 | 12.0 |
| 22 | 14.0 | 14.0 | 14.0 | 15.0 | 14.0 | 12.0 |
| 23 | 15.5 | 14.0 | 14.0 | 13.0 | 13.0 | 11.0 |
| 24 | 15.0 | 13.0 | 16.0 | 13.0 | 13.0 | 11.0 |
| 25 | 14.0 | 13.0 | 15.5 | 15.5 | 13.5 | 11.0 |
| 26 | 14.5 | 13.0 | 14.0 | 13.5 | 14.0 | 11.0 |
| 27 | 16.0 | 13.0 | 15.5 | 12.0 | 14.0 | 12.0 |
| 28 | 15.0 | 13.5 | 15.0 | 12.0 | 14.0 | 11.0 |
| 29 | 14.5 | 14.0 | 14.0 | 13.0 | 13.5 | 12.0 |
| 30 | 15.0 | 14.5 | 14.5 | 14.0 | 15.0 | 11.0 |
| Average | 15.4 | 13.7 | 15.0 | 13.2 | 14.4 | 11.3 |
| Stan dev | 6.65E−01 | 4.45E−01 | 6.66E−01 | 8.64E−01 | 6.71E−01 | 6.34E−01 |
| T test | 8.54E−17 | | 8.93E−13 | | 2.79E−25 | |
| Probability % | 100.00 | | 100.00 | | 100.00 | |
| % Difference | −12.4 | | −13.8 | | −26.6 | |
| Confidence Int | 0.0076 | 0.0051 | 0.0076 | 0.0099 | 0.0077 | 0.0073 |
| Range of Var min* | 15.38 | 13.68 | 14.97 | 13.16 | 14.34 | 11.33 |
| Range of Var max* | 15.39 | 13.69 | 14.99 | 13.18 | 14.36 | 11.34 |

*Range of variation among means of statistically significant differences at the 95% level using the confidence interval 'Dover' is a new and distinct variety of iceberg lettuce that most closely resembles the commercial variety 'Crusader'. It is a Vanguard type iceberg lettuce variety adapted to the fall harvest of the desert south west and Huron lettuce production regions of California and Arizona. It is large heading and large framed widely adapted variety, with improved heading characteristics, and improved resistance to tip burn and bolting and offers a larger planting and harvest window than like varieties. 'Dover' is distinct from 'Crusader' by three important traits: 1) it consistently produces larger size heads than 'Crusader'; 2) it has a consistently shorter core length; and 3) it has a significantly longer harvest period.

Because of its significantly longer harvest period compared to that of 'Crusader', 'Dover' is able to be planted and harvested through a longer time slot in the production season of the desert south west production region. Similar to 'Crusader', 'Dover' is adapted to the fall harvest in the desert south west and Huron production regions, but will consistently produce larger and heavier heads later into the harvest season. Whereas the plantings of 'Crusader' in the desert south west production region are recommended to stop on September 27$^{th}$, 'Dover' can continue to be planted through the first of October. Though this only represents a difference of roughly 5 days in planting the varieties, it actually represents a 15-day difference in harvest. This is because, during this time in the season, a one-day difference in the date of watering of the first seed germination can represent up to a 4-day difference in harvest. For example, if a field of lettuce is first watered on September 24$^{th}$ in the Yuma production region of the desert south west, it would likely reach market maturity on or about December 16$^{th}$. In contrast, a field first watered on September 25$^{th}$ would reach maturity on or about December 19$^{th}$. Thus, a field planted on October 2$^{nd}$ would likely reach maturity on or about January 2$^{nd}$. Therefore, the ability of 'Dover' to be planted into the first days of October extends the harvest window significantly beyond that of 'Crusader'. This is demonstrated in Table 2, where the relative head diameters of the two varieties are compared. Both varieties produce marketable head sizes through the September 25$^{th}$ water dates, but the head size of 'Crusader' drops off significantly in the trial watered on October 2$^{nd}$ whereas the head size of 'Dover' remains relatively consistent to that of the earlier plantings. The head diameter of 'Crusader' from the October 2$^{nd}$ water date is on average 11.3 cm, which is basically too small for commercial sale. In contrast, the head diameter of 'Dover' in this trial is over 14 cm, well within the size tolerances for commercial iceberg lettuce.

'Dover' is distinguished from 'Crusader' by the following characteristics as represented in Tables 1 and 2: 1) 'Dover' has a significantly shorter core length than 'Crusader' and 2) 'Dover' has a larger head diameter than 'Crusader'. This data is represented in Tables 1 and 2, and are statistically significant at the 95% confidence level, exhibiting a range of means for core length from 29.78 to 47.57 mm for 'Dover' and from 38.26 to 55.38 mm for 'Crusader'. The head diameter ranges from 14.34 to 15.39 cm for 'Dover' and from 11.33 to 13.69 cm for 'Crusader', using the 0.95 probability of generating confidence intervals that contains the means.

Although the foregoing invention has been described in some detail by way of illustration and examples for purposes of clarity and understanding, it will be obvious that certain modifications and alternative embodiments of the invention are contemplated, which do not depart from the spirit and scope of the invention as defined by the foregoing teachings and appended claims.

I claim:

1. *Lactuca sativa* seed designated as 'Dover' having ATCC Accession Number PTA-12097.

2. A *Lactuca sativa* plant produced by growing the seed of claim 1.

3. A lettuce head isolated from the plant of claim 2.

4. A *Lactuca sativa* plant having all the physiological and morphological characteristics of the *Lactuca sativa* plant of claim 2.

5. An $F_1$ hybrid *Lactuca sativa* plant having 'Dover' as a parent where 'Dover' is grown from the seed of claim 1.

6. Pollen of the plant of claim 2.

7. An ovule of the plant of claims 2.

8. Tissue culture of the plant of claim 2.

9. A method of selecting lettuce, comprising a) growing more than one plant from the seed of claim 1 b) selecting a plant from step a).

10. A selected lettuce plant selected by the method of claim 9.

11. A lettuce seed produced from the selected plant of claim 10.

* * * * *